US006568770B2

(12) United States Patent
Gonska et al.

(10) Patent No.: US 6,568,770 B2
(45) Date of Patent: May 27, 2003

(54) CLIMATIC CABINET

(75) Inventors: Gernot Gonska, Bad Vibel (DE); Thorsten Dick, Fulda (DE); Heiko Reinhardt, Hanau (DE)

(73) Assignee: Kendro Laboratory Products GmbH, Hanau (DE)

( * ) Notice: Subject to any disclaimer, the term of this patent is extended or adjusted under 35 U.S.C. 154(b) by 77 days.

(21) Appl. No.: 09/861,333

(22) Filed: May 18, 2001

(65) Prior Publication Data

US 2001/0043031 A1 Nov. 22, 2001

(30) Foreign Application Priority Data

May 19, 2000 (DE) .......................... 100 24 581

(51) Int. Cl.[7] ............................... G11B 17/22
(52) U.S. Cl. .................. 312/9.12; 312/306; 369/34.01; 369/36.01
(58) Field of Search .......................... 369/34.01, 36.01, 369/37.01, 38.01, 39.01; 312/9.1, 9.48, 9.32, 9.12, 9.9, 35, 223.1, 306, 304, 312, 319.5–319.8

(56) References Cited

U.S. PATENT DOCUMENTS

| 2,321,794 A | | 6/1943 | Braun | |
|---|---|---|---|---|
| 4,250,266 A | | 2/1981 | Wade | |
| 4,675,856 A | * | 6/1987 | Rudy et al. | 360/98.06 |
| 4,742,504 A | * | 5/1988 | Takasuka et al. | 369/30.45 |
| 4,815,055 A | * | 3/1989 | Fago, Jr. | 360/98.06 |
| 4,907,889 A | * | 3/1990 | Simone | 360/92 |
| 4,912,575 A | * | 3/1990 | Shiosaki | 360/71 |
| 4,981,409 A | * | 1/1991 | Hirose et al. | 414/223.01 |
| 5,220,548 A | * | 6/1993 | Nakatsukasa et al. | 369/30.45 |
| 5,266,272 A | | 11/1993 | Griner et al. | |
| 5,343,403 A | | 8/1994 | Beidle et al. | |
| 5,449,229 A | | 9/1995 | Aschenbrenner et al. | |
| 5,541,897 A | | 7/1996 | Baca et al. | |
| 5,622,470 A | * | 4/1997 | Schaefer et al. | 414/275 |
| 5,733,024 A | | 3/1998 | Slocum et al. | |
| 5,735,587 A | | 4/1998 | Malin et al. | |
| 6,129,428 A | | 10/2000 | Helwig et al. | |
| 6,400,659 B1 | * | 6/2002 | Kitaoka | 369/34.01 |

FOREIGN PATENT DOCUMENTS

| EP | 0 165 172 | 12/1985 |
|---|---|---|
| EP | 0 281 547 | 9/1988 |
| EP | 0 293 782 | 12/1988 |
| FR | 681488 | 1/1929 |
| WO | WO 92/14550 | 9/1992 |

* cited by examiner

Primary Examiner—Janet M. Wilkens
(74) Attorney, Agent, or Firm—Baker & Hostetler LLP

(57) ABSTRACT

A climatic cabinet with at least one door, having a storage station with at least one object storage device, which exhibits several storage locations arranged one on top of the other, and having a transport device for feeding objects to the object storage locations, wherein the transport device has an object receiver, wherein the object receiver is secured to a vertical carriage in such a way that it can be moved vertically and horizontally, and wherein the storage station and transport device are arranged on mounting plates. The functionality of the climatic cabinet and its functionality are achieved through improvements in the transport device.

27 Claims, 5 Drawing Sheets

CLIMATIC CABINET

CROSS-REFERENCE TO RELATED APPLICATIONS

This application claims priority to German Patent Application No. 100 24 581.1, filed May 19, 2000, which application is incorporated herein by specific reference.

BACKGROUND OF THE INVENTION

1. The Field of the Invention

The invention relates to a climatic cabinet with at least one door, having a storage station with at least one object storage device, which exhibits several storage locations arranged one on top of the other, and having a transport device for feeding objects to the object storage locations, wherein the transport device has an object receiver, wherein the object receiver is secured to a vertical carriage in such a way that it can be moved vertically and horizontally, and wherein the storage station and transport device are arranged on mounting plates.

2. The Relevant Technology

Climatic cabinets such as that disclosed in U.S. Pat. No. 6,129,428 are known in the art. The U.S. Pat. No. 6,129,428 patent discloses climatic cabinets in which objects, e.g., microtiter plates or object support plates, hereinafter and generally referred to as objects, are introduced into and extracted from magazines by means of a transport system. The magazines are designed as a carrousel, i.e., rotatable, wherein a transport system is allocated to one or more such magazines. The transport system enables the vertical and horizontal movement of objects, wherein horizontal mobility takes the form of both translational and rotational movement. Numerous drives, such as electric motors, are required to execute the sequence of movements.

BRIEF SUMMARY OF THE INVENTION

An object of the present invention is to improve the functionality of known climatic cabinets and improve their reliability.

This object is achieved for a climatic cabinet of the kind described at the outset by arranging the storage station between the door and transport device located inside the climatic cabinet, and by arranging the mounting plate that carries the storage station inside the climatic cabinet higher than the mounting plate that carries the transport device. As a result, the height of the object storage device can be optimally utilized with regard to the arrangement of object storage locations, since dead spaces in the lower portion of the storage device can be avoided.

In a second embodiment of the invention, the object receiver is linked with a counterweight by a moveable connecting element routed over a reversing unit arranged in the upper area of the vertical carriage. This counterbalances a portion of the mass to be moved vertically, so that less energy is required for the vertical movement. Accordingly, the drives for the vertical positioning, e.g., electric motors, can be smaller.

Another embodiment of the invention is characterized in that the object receiver has guide rails for guiding the object to be transported, and at least one microswitch with a moveable switching element, which projects into the area of the object to be received by the object receiver. The microswitch triggers a signal by moving the switching element in a receive position of the object in the object receiver. When introducing the object into the object receiver, the object is guided via guide rails, and hence in a defined manner. As it moves into the stipulated position in or on the object receiver, the object pushes the moveable switching element out of this area. At this time, the microswitch releases a signal in a known manner. The switching element can have various known designs. For example, the switching element can execute a movement along a straight line or curved path. The advantage to such microswitches is that they can be used under conditions where conventional optical detection systems fail, for example at high temperatures in conjunction with high atmospheric humidity. In this case, the guide rails ensure that the microswitch can be reliably triggered, and that the object moves in the stipulated manner without being forced into an unintended direction by the microswitch. The microswitch can be situated either horizontally to the side inside the object receiver or under the space provided for receiving the object in the object receiver. This ensures a reliable detection of the correct deposition of the object.

Another embodiment of the present invention is characterized in that the object receiver has a horizontally moveable blade for receiving at least one object, a motor drives the blade, and the motor is situated on the blade. This type of arrangement permits a relatively small design, and the drive is simple to implement. As a result, the service opening can be small so as not to significantly impair the climate inside the climatic cabinet. In addition, the functional reliability of the object receiver is increased.

According to the invention, the individual embodiments disclosed herein can also be combined as desired.

Advantageous embodiments of the invention are indicated in the subclaims. In particular, it is desirable to connect both mounting plates by means of an adapter. Both mounting plates are preferably made out of a single, offset base plate for easier handling. It is desirable to have a gap, between the mounting plate carrying the storage station and a lower edge of the door, through which the service personnel can reach. This provides direct access to a water trough that, in practice, is often arranged under the object storage device. As a result, the water trough can be cleaned out without extensive disassembly. In particular, when the difference in height between the two mounting plates is at least as great as the height of the object receiver, the latter can be moved under the object storage device so that object storage locations can also be provided right in the lower area of the object storage device. This increases the number of possible object storage locations, and hence the climatic cabinet efficiency. This configuration also avoids unused space.

One especially simple construction of the transport device is achieved by allocating the drives for the object receiver to the object receiver itself. In addition, it is desirable to provide a service opening on the side opposite the door as an access for at least part of the object receiver. As a result, the objects can be transported into or out of the climatic cabinet through the service hole opening, that can have relatively small dimensions, without having to open the generally large-sized door which is often used essentially for assembly and maintenance. In this case, the service opening is generally only big enough to enable delivery of objects from outside to the inside. In this configuration it makes no difference whether the object is transported from a transport device arranged inside the climatic cabinet to the outside, or from the outside to the inside, or whether this transport takes place from a transport device located outside the climatic cabinet. For space considerations, the transport device of the climatic cabinet according to the present invention is preferably situated in the climatic cabinet itself. This also results in a better functionality and simpler construction.

In addition, it is desirable for the moveable connecting element linking the counterweight and object receiver to be designed as a rope, belt or chain. In terms of length, the connecting element can be dimensioned in such a way that the connecting element does not take the object receiver over its highest attachment point on the vertical carriage when the counterweight is in its lower end position. This increases the reliability of vertical movement by the object receiver. The object receiver can easily be removed form the upper end of the vertical carriage by hand. The reversing unit is preferably situated on the vertical carriage or in its upper area. It can then simultaneously serve as a safety element to prevent an unintended detachment of the object receiver from the vertical carriage. The reversing unit is preferably fixed in place with a quick acting closure, e.g., a single screwed fitting. The reversing unit can be secured to the vertical carriage itself, or to a casing section near the vertical carriage.

BRIEF DESCRIPTION OF THE DRAWINGS

An embodiment of the invention will be described in greater detail below using drawings in which.

DETAILED DESCRIPTION OF THE PREFERRED EMBODIMENTS

The basic structure of climatic cabinets is generally known. In particular U.S. Pat. No. 6,129,428, whose content is incorporated herein by specific reference, discloses the structure of climatic cabinets with a transport system and object storage devices.

Figure 1:
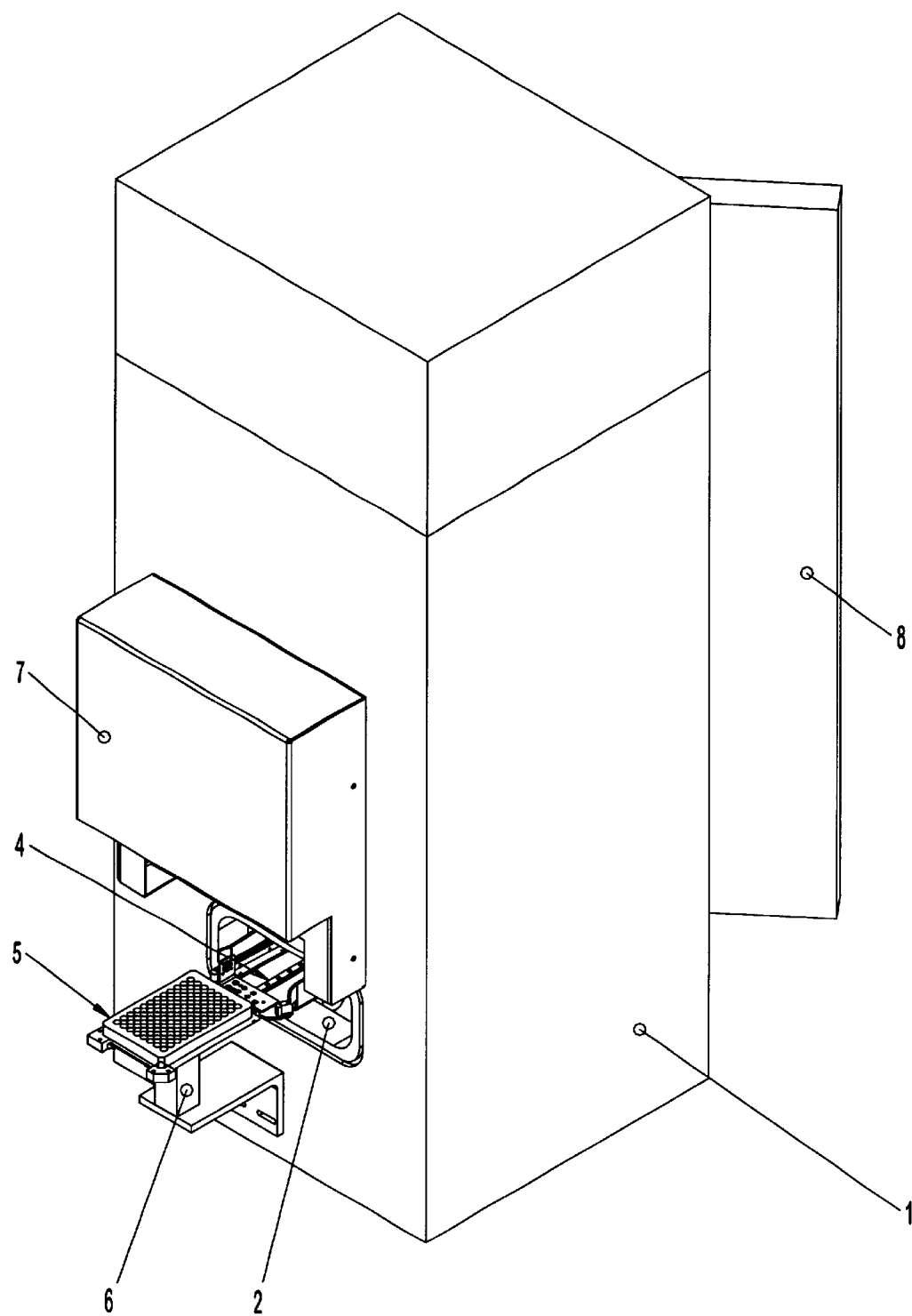
FIG. 1 is a rear perspective view of a climatic cabinet.

FIG. 1 shows a climatic cabinet 1 with a service opening 2. A transport device 3 situated inside the climatic cabinet 1 (compare FIG. 2) transports an object 5 via its object receiver 4 into or out of the climatic cabinet 1 through service opening 2. A delivery station 6 situated outside the climatic cabinet 1 in front of the service opening 2 enables the delivery of the object 5 to a handling device located on the outside. A sealing mechanism 7 for the service opening 2 is provided above the service opening 2, which releases the service opening 2 for the through transport of objects 5.

Figure 5:
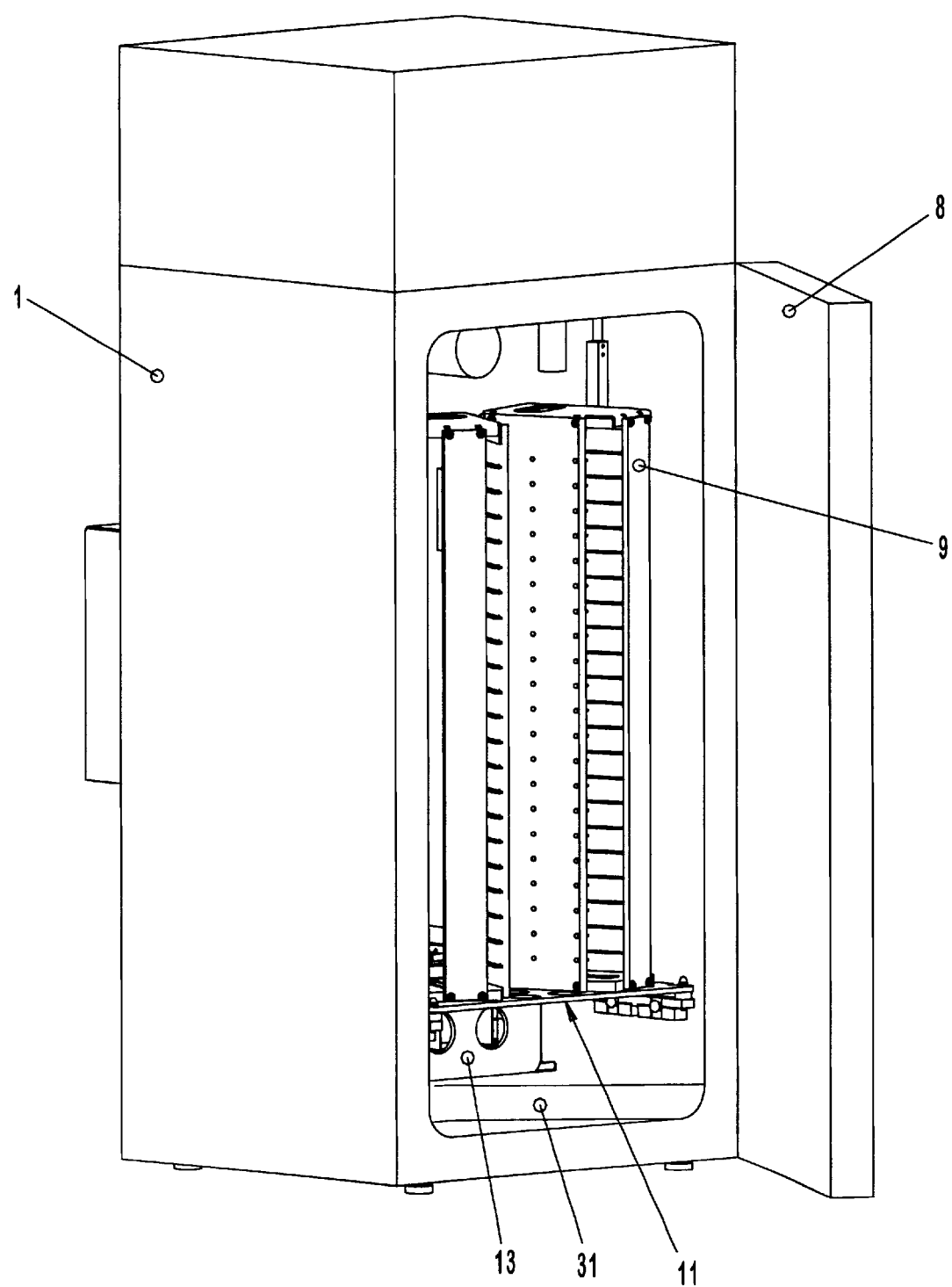
FIG. 5 is a front perspective view of the climatic cabinet shown in FIG. 1.

The front side of the climatic cabinet 1 has a door 8, which is used for the assembly and removal of object storage devices 9 (FIG. 2), and also for cleaning or maintaining the climatic cabinet 1. A water trough 31 (FIG. 5) is arranged inside the climatic cabinet 1 for humidity control under a storage station 10. The storage station 10 is situated on a mounting plate 11 between the transport device 3 and door 8. The mounting plate 11 has a sufficient gap to the lower edge of the door 8, so that service personnel can easily reach into the water trough 31 for cleaning purposes (FIG. 5). The water trough 31 can be stand-alone, or designed as a component of the floor of the interior wall of the climatic cabinet 1. The floor surface of the water trough 31 can have a slight gradient, preferably toward the rear.

Figure 2:
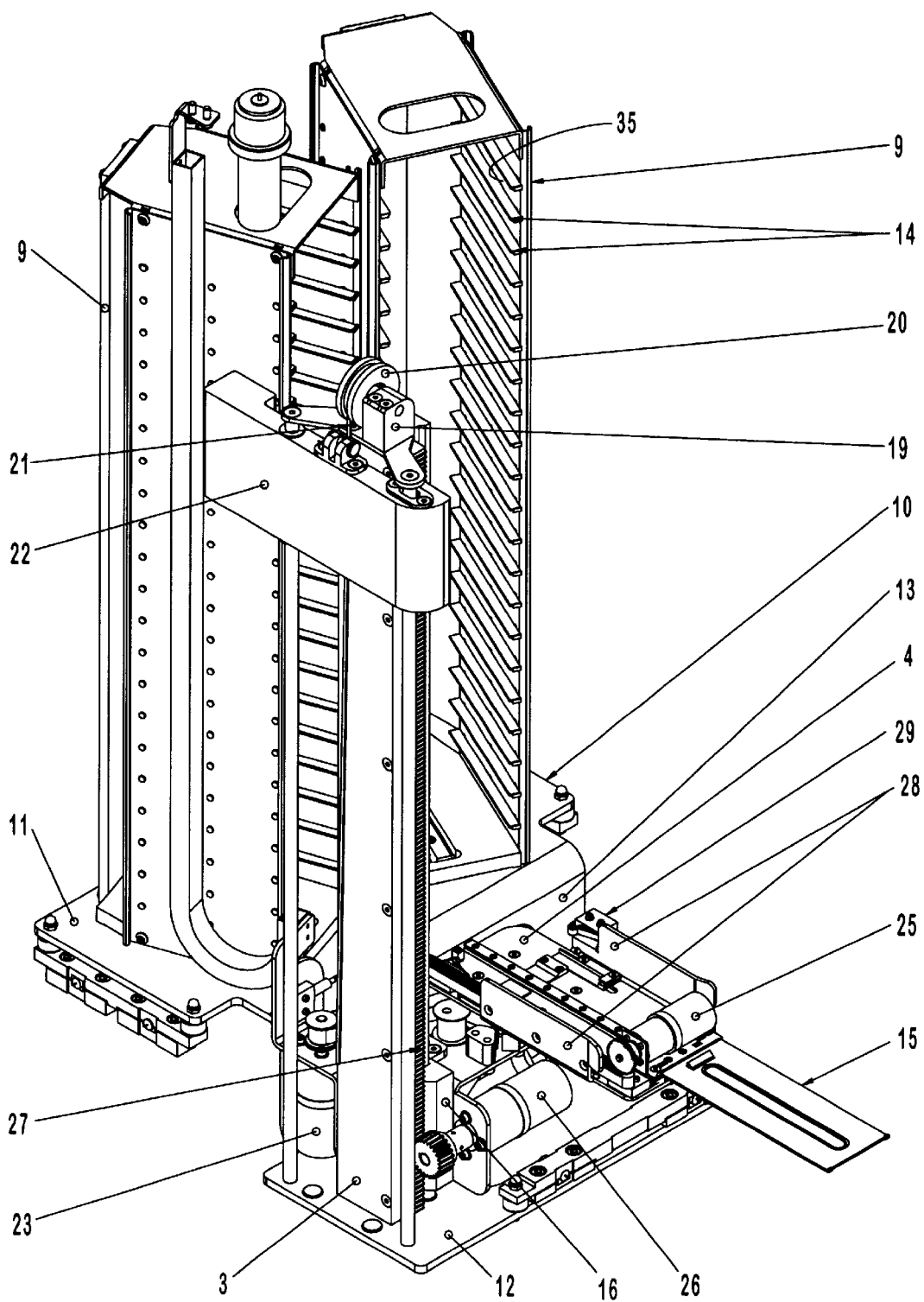
FIG. 2 is a left side perspective view of a transport device for installation in the climatic cabinet of FIG. 1.
Figure 3:
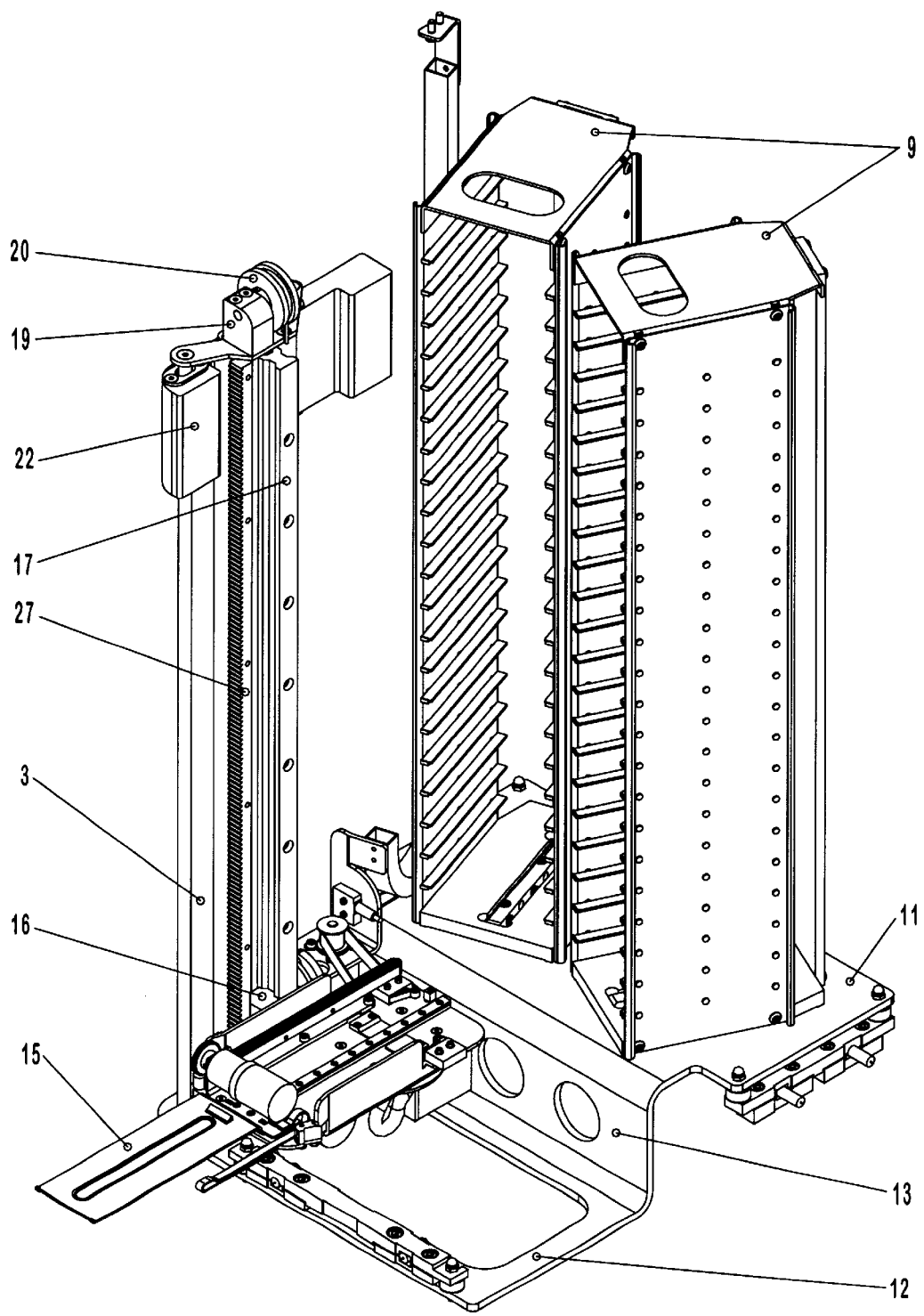
FIG. 3 is a right side perspective view of the transport device shown in FIG. 2.

The transport device 3 shown on FIGS. 2 and 3 is also set up on a mounting plate 12. The mounting plate 12 is connected with the mounting plate 11 by an adapter 13. In one embodiment, the two mounting plates 11, 12 and adapter 13 consist of a uniform piece of material, e.g., sheet steel. The mounting plate 12 is built deeper into the climatic cabinet 1 than the mounting plate 11, so that the complete object receiver 4 essentially lies under the object storage devices 9. The object storage devices 9 have numerous object storage locations 35 formed by carrier rails 14 for the storage of objects 5.

The objects 5 to be transported are loaded on a carriage 15 of the object receiver 4 and again released. To this end, the object receiver 4 of the transport device 3 can be moved horizontally and vertically. The horizontal movement takes the form of a rotational or pivoting motion, and a linear motion of the carriage 15. The vertical movement ensues on a vertical carriage 18, wherein a guide profile 17 of the vertical carriage 18 engages a guide profile 16 of the object receiver 4. A reversing unit 19 with a reversing roller 20 is arranged on the top of the vertical carriage 18. The reversing roller 20 carries a rope 21, to which the object receiver 4 and a counterweight 22 are secured. The reversing unit 19 is arranged in such a way as to simultaneously form an end stop for the object receiver 4 and counter weight 22. It can be removed by loosening a screw, so that the object receiver 4 can easily be separated from the vertical carriage 18. The length of the rope 21 is such that the object receiver 4 does not reach the end stop in its top position if the counterweight 22 is in its bottom position. This makes it impossible to damage the device by unintentionally going too far.

Figure 4:
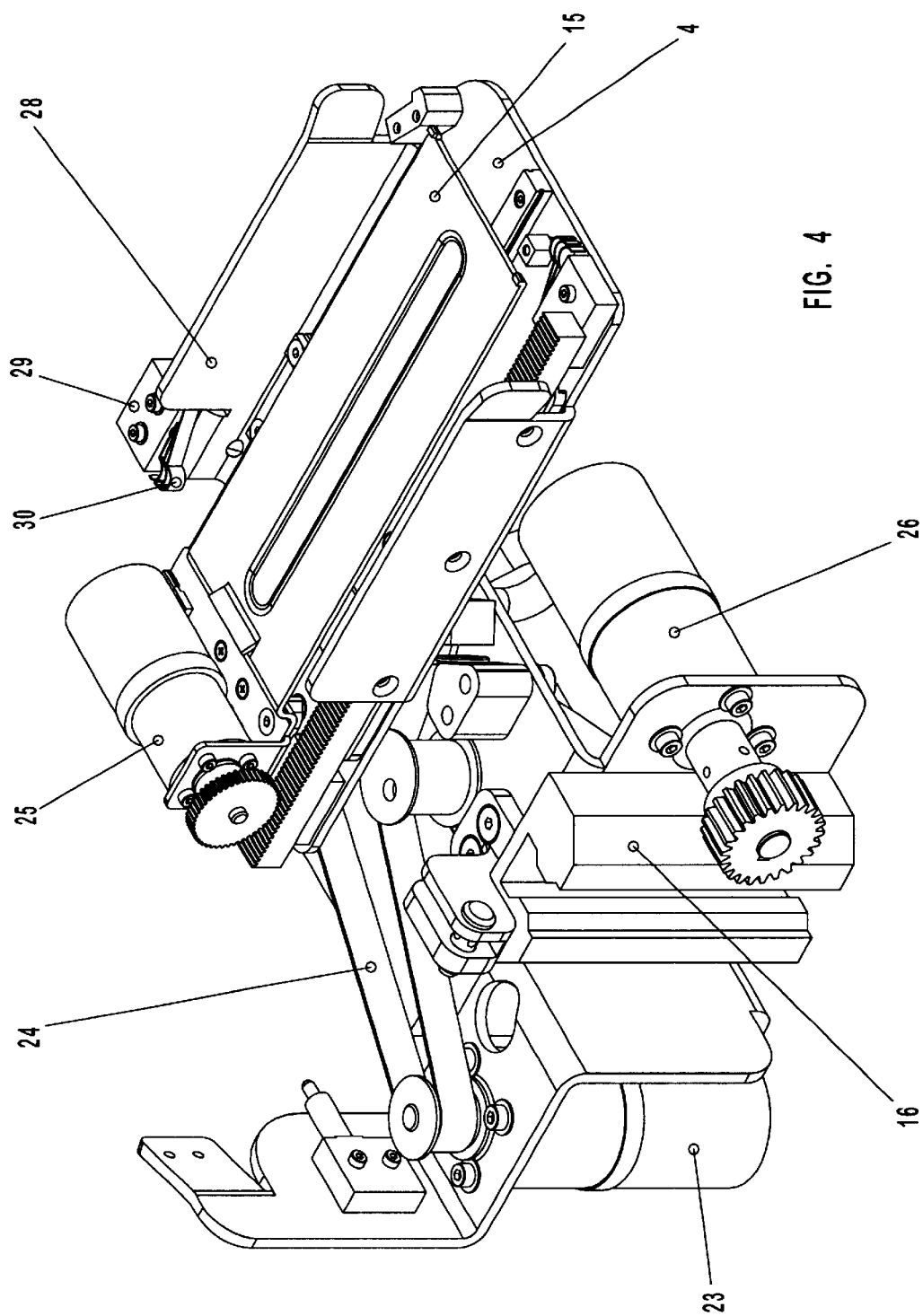
FIG. 4 is a perspective view of an object receiver of the transport device shown in FIGS. 2 and 3.

FIG. 4 shows the object receiver 4 in detail. All drives present for movement purposes are arranged on the object receiver 4, which simplifies assembly and maintenance. The structural outlay is also reduced. A motor 23 uses a belt 24 to impart a rotational motion to the carriage 15. A motor 25 situated directly on the carriage 15 initiates the linear movement of the carriage 15 for receiving and releasing objects 5. The carriage 15 either passes through the service opening 2 or into the object storage locations 35 between the carrier rails 14. Another motor 26 uses a rack 27 to enable vertical movement along the vertical carriage 18.

The object receiver 4 also has guide rails 28 for laterally guiding the object(s) 5. The guide rails 28 ensure that the objects 5 are precisely received and released, and also stably positioned on the object receiver 4. A microswitch 29 is arranged to a side of the carriage 15, with a moveable switching element 30. The moveable switching element 30 projects into the space formed by the guide rails 28 and carriage 15, which is intended to receive the objects 5. Movable switching element 30 is actuated as soon as an object 5 has been deposited on the carriage 15, and the carriage 15 has been driven into position intended for the rotational motion on the object receiver 4. This causes a signal to be released, indicating that an object 5 is situated on the object receiver 4. The signal can be further processed as part of a control program to initiate continued transport to a predetermined spot within the object storage devices 9.

The object storage devices 9 shown on the figures are essentially fixed in place. However, it is also possible for the object storage devices 9 or storage station 10 to be moveable, e.g., to enable a better adaptation to the transport device 3. The receiving capacity of the storage station 10 can also be increased. For example, the object storage devices 9 shown on the figures or the storage station 10 can be replaced with carrousel storage devices or storage stations of the kind disclosed in U.S. Pat. No. 6,129,428, which has been incorporated herein by specific reference.

What is claimed is:

1. A climatic cabinet with at least one door, having a storage station with at least one object storage device, which exhibits several storage locations arranged one on top of the other, and having a transport device for feeding objects to the object storage locations, wherein the transport device has an object receiver, wherein the object receiver is secured to a vertical carriage in such a way that it can be moved vertically and horizontally, and wherein the storage station and transport device are arranged on mounting plates, characterized in that the storage station (10) is situated between the door (8) and the transport device (3) arranged inside the climatic cabinet (1), and that the mounting plate (11) that carries the storage station (10) is situated higher in the climatic cabinet than the mounting plate (12) that carries the transport device (3).

2. The climatic cabinet according to claim 1, characterized in that both mounting plates (11; 12) are connected with each other by an adapter (13).

3. The climatic cabinet according to claim 1, characterized in that a gap is formed between the mounting plate (11) that carries the storage station (10) and the lower edge of the door (8), through which service personnel can reach.

4. The climatic cabinet according to claim 1, characterized in that the difference in height between the two mounting plates (11; 12) is at least as great as the height of the object receiver (4).

5. The climatic cabinet according to claim 1, characterized in that the drives for the object receiver (4) are situated on the object receiver.

6. The climatic cabinet according to claim 1, characterized in that a service opening (2) is provided on the side of the climatic cabinet opposite the door (8) as an access for at least part of the object receiver (4).

7. The climatic cabinet according to claim 1, characterized in that the transport device (3) is arranged inside the climatic cabinet (1).

8. A climatic cabinet with at least one door, having a storage station with at least one object storage device, which exhibits several storage locations arranged one on top of the other, and having a transport device for feeding objects to the object storage locations, wherein the transport device has an object receiver, wherein the object receiver is secured to a vertical carriage in such a way that it can be moved vertically and horizontally, and wherein the storage station and transport device are arranged on mounting plates, characterized in that the object receiver (4) is linked with a counterweight (22) via a moveable connecting element (21), which is routed over a reversing unit (19) arranged in the upper area of the vertical carriage (18), characterized in that both mounting plates (11; 12) are connected with each other by an adapter (13).

9. The climatic cabinet according to claim 8, characterized in that a gap is formed between the mounting plate (11) that carries the storage station (10) and the lower edge of the door (8), through which service personnel can reach.

10. The climatic cabinet according to claim 8, characterized in that the difference in height between the two mounting places (11; 12) is at least as great as the height of the object receiver (4).

11. The climatic cabinet according to claim 8, characterized in that the drives for the object receiver (4) are situated on the object receiver.

12. The climatic cabinet according to claim 8, in that a service opening (2) is provided on the side of the climatic cabinet opposite the door (8) as an access for at least part of the object receiver (4).

13. The climatic cabinet according to claim 8, characterized in that the moveable connecting element (21) consists of rope, belt or chain.

14. The climatic cabinet according to claim 8, characterized in that the transport device (3) is arranged inside the climatic cabinet (1).

15. A climatic cabinet with at least one door, having a storage station with at least one object storage device, which exhibits several storage locations arranged one on top of the other, and having a transport device for feeding objects to the object storage locations, wherein the transport device has an object receiver, wherein the object receiver is secured to a vertical carriage in such a way that it can be moved vertically and horizontally, and wherein the storage station and transport device are arranged on mounting plates, characterized in that the object receiver (4) is linked with a counterweight (22) via a moveable connecting element (21), which is routed over a reversing unit (19) arranged in the upper area of the vertical carriage (18), characterized in that the reversing unit (19) is arranged on the vertical carriage (18) and is locked in place with a quick acting closure.

16. A climatic cabinet with at least one door, having a storage station with at least one object storage device, which exhibits several storage locations arranged one on top of the other, and having a transport device for feeding objects to the object storage locations, wherein the transport device has an object receiver, wherein the object receiver is secured to a vertical carriage in such a way that it can be moved vertically and horizontally, and wherein the storage station and transport device are arranged on mounting plates, characterized in that the object receiver (4) has guide rails (28) for guiding the transported object (5), and has at least one microswitch (29) with a moveable switching element (30) that projects into the area of the object (5) to be received by the object receiver (4), wherein the microswitch (29) triggers a signal when the object (5) is in a receive position on the object receiver (4) characterized in that a gap is formed between the mounting plate (11) that carries the storage station (10) and the lower edge of the door (8), through which service personnel can reach.

17. The climatic cabinet according to claim 16, characterized in that both mounting plates (11; 12) are connected with each other by an adapter (13).

18. The climatic cabinet according to claim 16, characterized in that the difference in height between the two mounting plates (11; 12) is at least as great as the height of the object receiver (4).

19. The climatic cabinet according to claim 16, characterized in that the drives for the object receiver (4) are situated on the object receiver.

20. The climatic cabinet according to claim 16, characterized in that a service opening (2) is provided on the side of the climatic cabinet opposite the door (8) as an access for at least part of the object receiver (4).

21. The climatic cabinet according to claim 16, characterized in that the transport device (3) is arranged inside the climatic cabinet (1).

22. A climatic cabinet with at least one door, having a storage station with at least one object storage device, which exhibits several storage locations arranged one on top of the other and having a transport device for feeding objects to the object storage locations, wherein the transport device has an object receiver, wherein the object receiver is secured to a vertical carriage in such a way that it can be moved vertically and horizontally, and wherein the storage station and transport device are arranged on mounting plates, characterized in that the object receiver (4) has a horizontally moveable blade (15) configured for receiving at least one object (5), the blade (15) being driven by a motor (25), and that motor (25) being situated on the blade (15), characterized in that the difference in height between the two mounting plates (11; 12) is at least as great as the height of the object receiver (4).

23. The climatic cabinet according to claim 22, characterized in that both mounting plates (11; 12) are connected with each other by an adapter (13).

24. The climatic cabinet according to claim 22, characterized in that a gap is formed between the mounting plate (11) that carries the storage station (10) and the lower edge of the door (8), through which service personnel can reach.

25. The climatic cabinet according to claim 22, characterized in that the drives for the object receiver (4) are situated on the object receiver.

26. The climatic cabinet according to claim 22, characterized in that a service opening (2) is provided on the side of the climatic cabinet opposite the door (8) as an access for at least part of the object receiver (4).

27. The climatic cabinet according to claim 22, characterized in that the transport device (3) is arranged inside the climatic cabinet (1).

* * * * *